(12) United States Patent
Carson

(10) Patent No.: US 7,395,695 B2
(45) Date of Patent: Jul. 8, 2008

(54) APPARATUS FOR TESTING LENGTHS OF PIPE

(75) Inventor: Glenn Carson, Point Edward (CA)

(73) Assignee: Car-Ber Investments Inc., Point Edward (CA)

( * ) Notice: Subject to any disclaimer, the term of this patent is extended or adjusted under 35 U.S.C. 154(b) by 0 days.

(21) Appl. No.: 11/469,548

(22) Filed: Sep. 1, 2006

(65) Prior Publication Data

US 2007/0017279 A1    Jan. 25, 2007

Related U.S. Application Data

(63) Continuation of application No. PCT/CA2005/000319, filed on Mar. 2, 2005.

(60) Provisional application No. 60/548,960, filed on Mar. 2, 2004.

(51) Int. Cl.
*G01M 3/28* (2006.01)
*G01N 7/00* (2006.01)

(52) U.S. Cl. ............... 73/40.5 R; 73/49.1; 73/49.5; 73/49.8

(58) Field of Classification Search .......... 73/49.1, 73/49.5, 40.5 R, 49.6, 49.8
See application file for complete search history.

(56) References Cited

U.S. PATENT DOCUMENTS

| 4,067,228 | A | * | 1/1978 | Elle et al. | .................. 73/49.1 |
| 4,189,938 | A | * | 2/1980 | Heim | .................. 73/40.7 |
| 4,382,379 | A | * | 5/1983 | Kelly | .................. 73/46 |

FOREIGN PATENT DOCUMENTS

| CA | 2345335 A1 | 3/2000 |
| DE | 1220171 B | 6/1966 |
| EP | 0 727 651 B1 | 10/2002 |

* cited by examiner

*Primary Examiner*—Daniel S Larkin
(74) *Attorney, Agent, or Firm*—Blake, Cassels & Graydon LLP; Santosh K. Chari

(57) ABSTRACT

A pipe testing apparatus includes a mandrel adapted for insertion within the pipe and two sealing devices connected to the mandrel and adapted to seal opposite ends of the pipe to create an annular space between the mandrel, the pipe, and the sealing devices. The apparatus further includes one or more ports for filling the annular space with a pressurized fluid and a pressure gauge for monitoring the pressure within the annular space. At least one of the sealing devices includes a combination of a sealing ring and a force applying ring, which forces the sealing ring to bear against one end of the pipe to from a seal. The mandrel is provided with stops for preventing the at least one sealing device from moving axially away from the pipe.

22 Claims, 7 Drawing Sheets

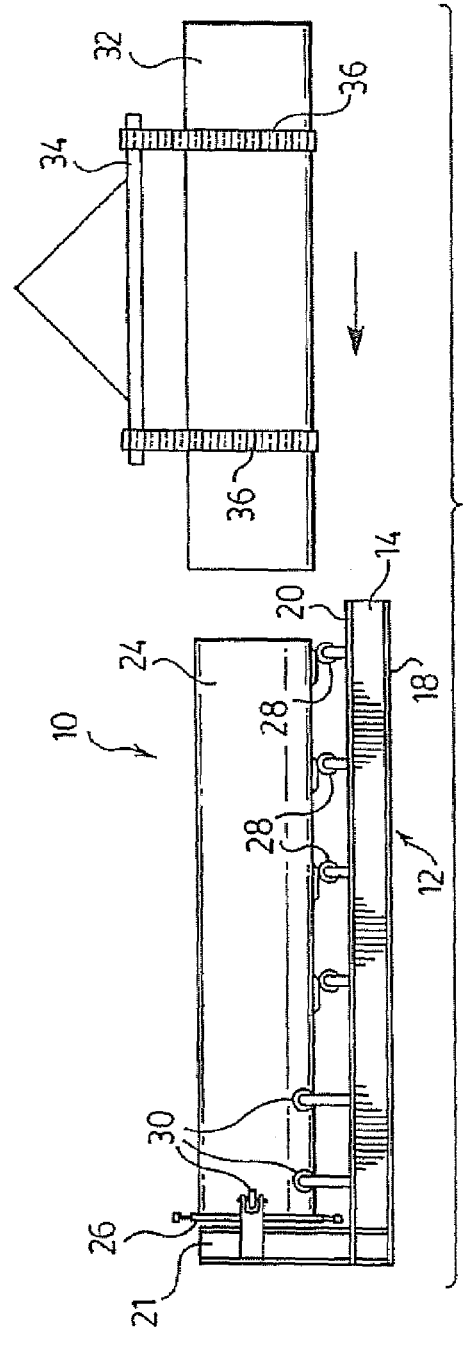
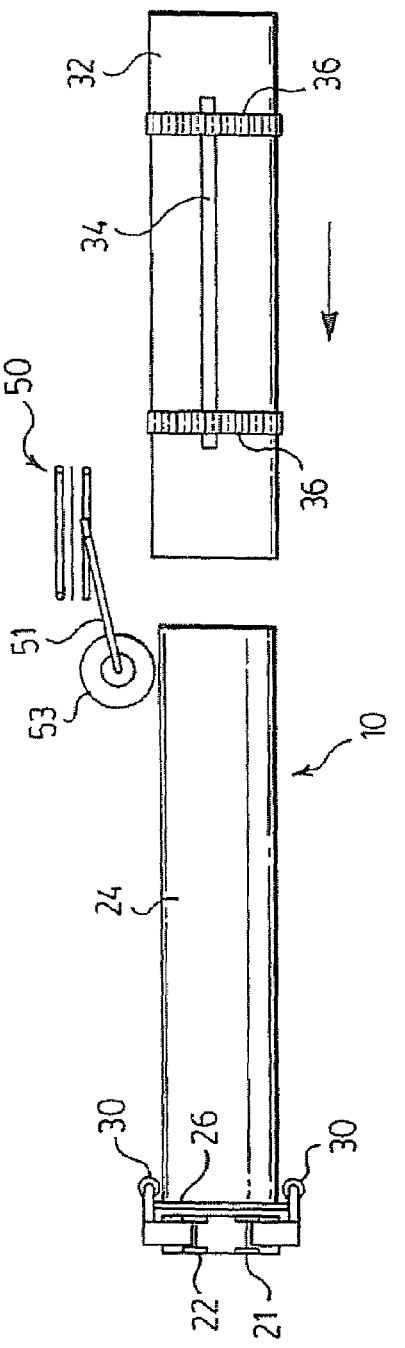

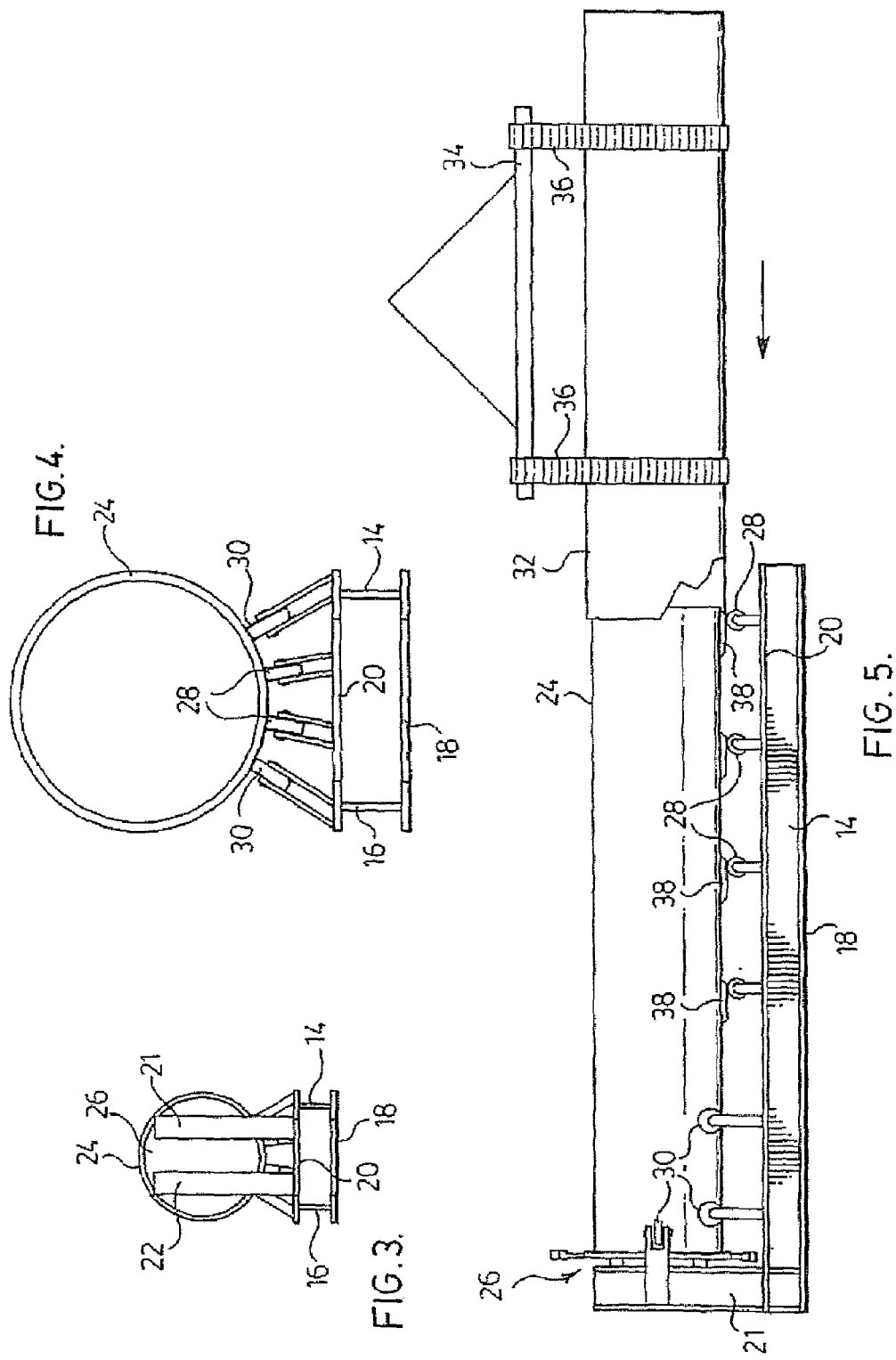

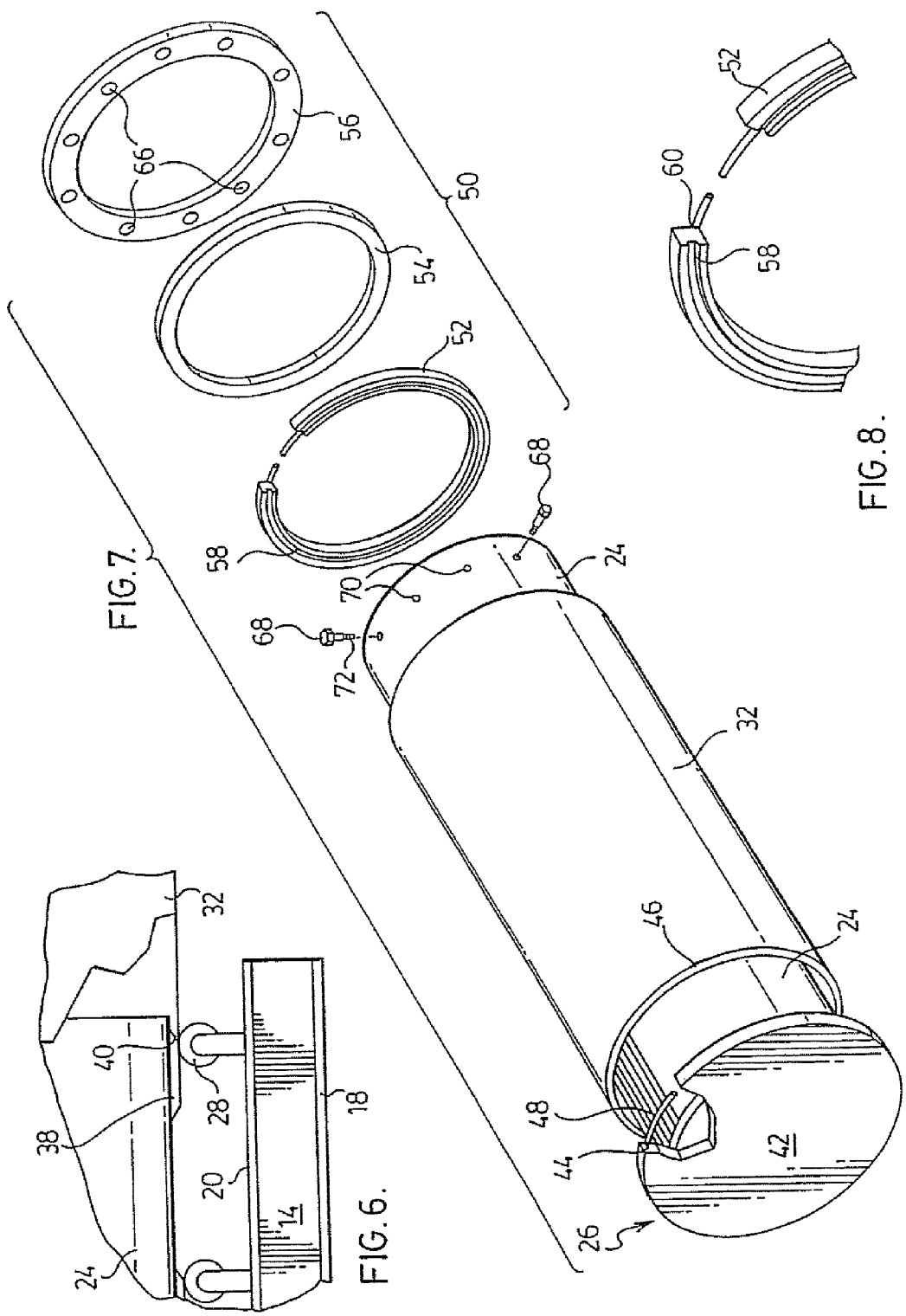

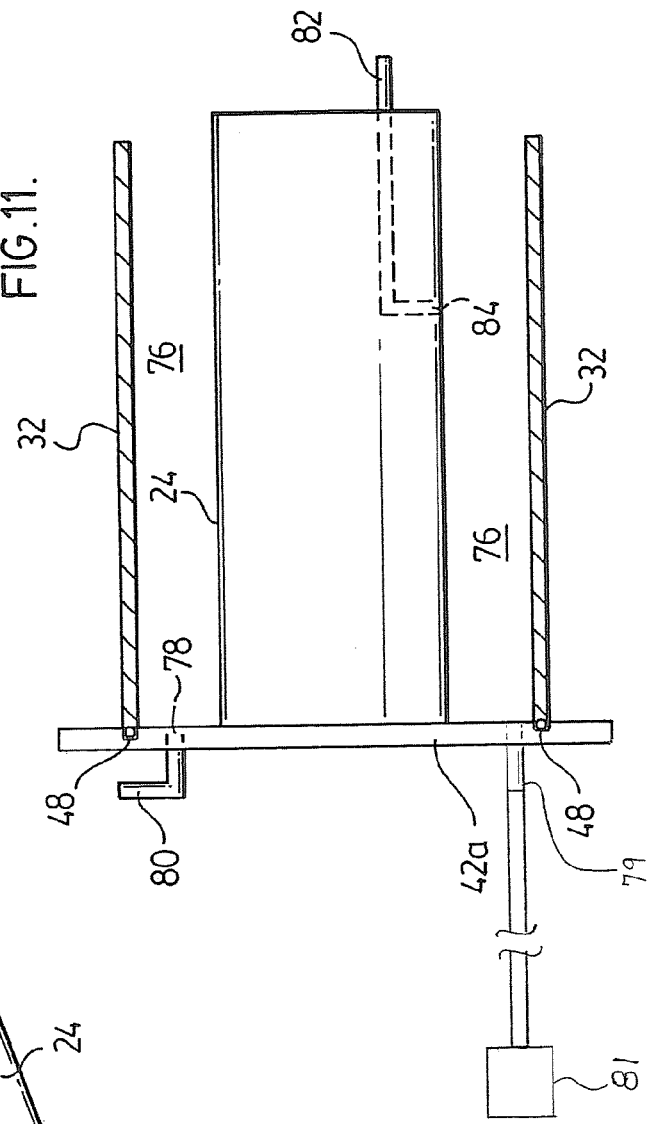
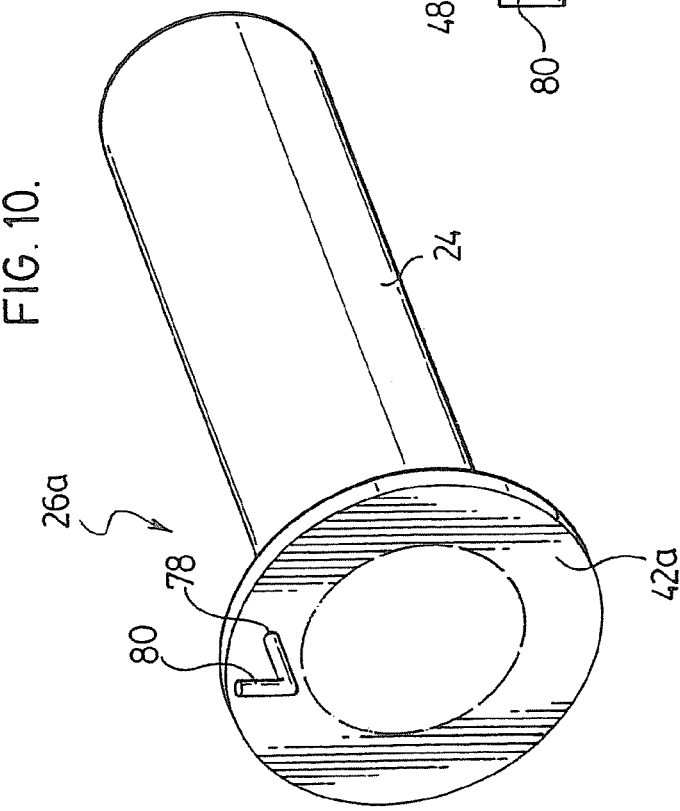

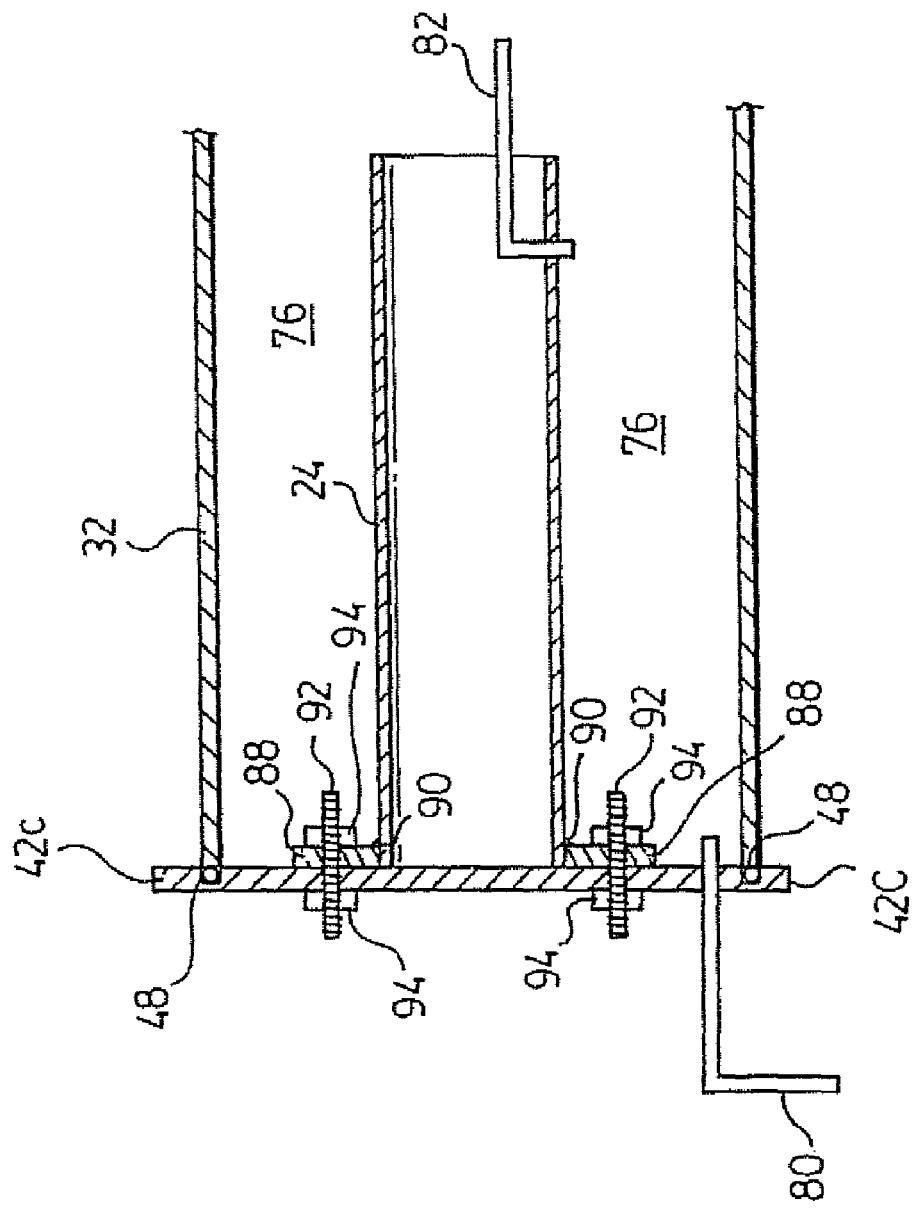

APPARATUS FOR TESTING LENGTHS OF PIPE

CROSS REFERENCE TO PRIOR APPLICATIONS

This application is a Continuation of PCT application number PCT/CA2005/000319 filed Mar. 2, 2005, which claims priority from U.S. Provisional application No. 60/548,960, filed Mar. 2, 2004. The entire contents of all such applications are incorporated herein by reference.

FIELD OF THE INVENTION

The present invention relates to apparatus for testing the integrity of pipes. More specifically, the invention relates to apparatus for efficiently testing lengths of pipe for structural defects.

BACKGROUND OF THE INVENTION

Pipes and other such conduits are commonly used in many applications for conveying fluid materials between locations. In order to ensure safety, it is common to conduct integrity tests on pipes to identify any cracks or other such openings through which the fluid being conveyed may leak. These cracks may result from defective welds on the pipe or from a defect in the tube manufacturing process. Pipe integrity testing is particularly important in situations where the pipe is used to convey flammable or toxic substances or when the pipe is conveying fluids under high pressure.

Various apparatus and methods are known in the art for testing pipes. In some of these known methods, a pipe section is simply filled with a typically incompressible fluid and pressurized while monitoring the pressure within the pipe. Any pressure drop is indicative of a leak in the pipe wall. Although effective, these known methods are inefficient since they require the entire volume of the pipe to be filled and pressurized, which is problematic when the pipe volume is large due to either a large diameter or a long length.

The prior art provides various types of pipe testing devices such as those taught in the following U.S. Pat. Nos. 6,463,791; 6,131,441; and, 5,844,127 (all of which share a common inventor with the present invention). Although these devices have proven effective in conducting tests on sections of pipe, there exists a need for an apparatus that efficiently tests lengths of pipe. Such a device is taught in U.S. Pat. No. 4,067,228. This reference provides an apparatus having a mandrel for insertion within a pipe segment to create an annular space between the inner pipe wall and the outer surface of the mandrel. In order to conduct the integrity test, a small volume of fluid is injected in the annular space and pressurized. Although providing an efficient test method, the apparatus of this reference is quite complicated and difficult to move from one location to another. Further, this reference does not provide a means of testing curved sections of pipe.

Thus, a need exists for a more efficient apparatus for testing the integrity of sections of pipes.

SUMMARY OF THE INVENTION

In one embodiment, the present invention provides an apparatus for testing the integrity of a pipe, said pipe having a length and first and second openings, the apparatus comprising:

a mandrel adapted to be inserted into the pipe, said mandrel having a length longer than the length of the pipe whereby said mandrel extends beyond said first and second openings of the pipe;

said mandrel having first and second ends, wherein said first end is proximal to the first opening of said pipe and said second end is proximal to the second opening of said pipe;

a first sealing device adapted to be secured to the first end of said mandrel for sealing said first opening;

a second sealing device adapted to be secured to the second end of said mandrel for sealing said second opening;

whereby a generally annular space is created between said mandrel, said pipe, and said first and second sealing devices;

one or more ports for filling said annular space with a pressurizing fluid or for voiding said annular space of air or said fluid; and, a means for monitoring the pressure within said annular space.

In another embodiment, the invention provide an apparatus as described above but wherein at least one of said first and second sealing devices comprises:

an annular sealing ring, coaxially provided over said mandrel adjacent one end of said pipe, said sealing ring having an outer diameter greater than the diameter of said pipe; and, a force applying ring, coaxially provided over said mandrel adjacent said sealing ring and opposite from said pipe, for forcing said sealing ring towards said pipe.

BRIEF DESCRIPTION OF THE DRAWINGS

These and other features of the preferred embodiments of the invention will become more apparent in the following detailed description in which reference is made to the appended drawings wherein:

FIG. 1 is a side elevation of a testing apparatus according to an embodiment of the invention.

FIG. 2 is a top view of the apparatus of FIG. 1.

FIG. 3 is an end elevation of a first end of the apparatus of FIG. 1.

FIG. 4 is an end elevation of the apparatus of FIG. 1 through section A-A.

FIG. 5 is a side elevation of the testing apparatus of FIG. 1 in combination with a pipe to be tested.

FIG. 6 is a partial side elevation detail of FIG. 5.

FIG. 7 is an exploded perspective view of the mandrel of the invention in combination with the mandrel.

FIG. 8 is a partial perspective view of the sealing ring of FIG. 7.

FIG. 10 is a perspective view of an embodiment of the first sealing device.

FIG. 11 is a side cross sectional view of another embodiment of the invention.

FIG. 13 is a side cross sectional view of another embodiment of the invention.

DESCRIPTION OF THE PREFERRED EMBODIMENTS

Figure 9:
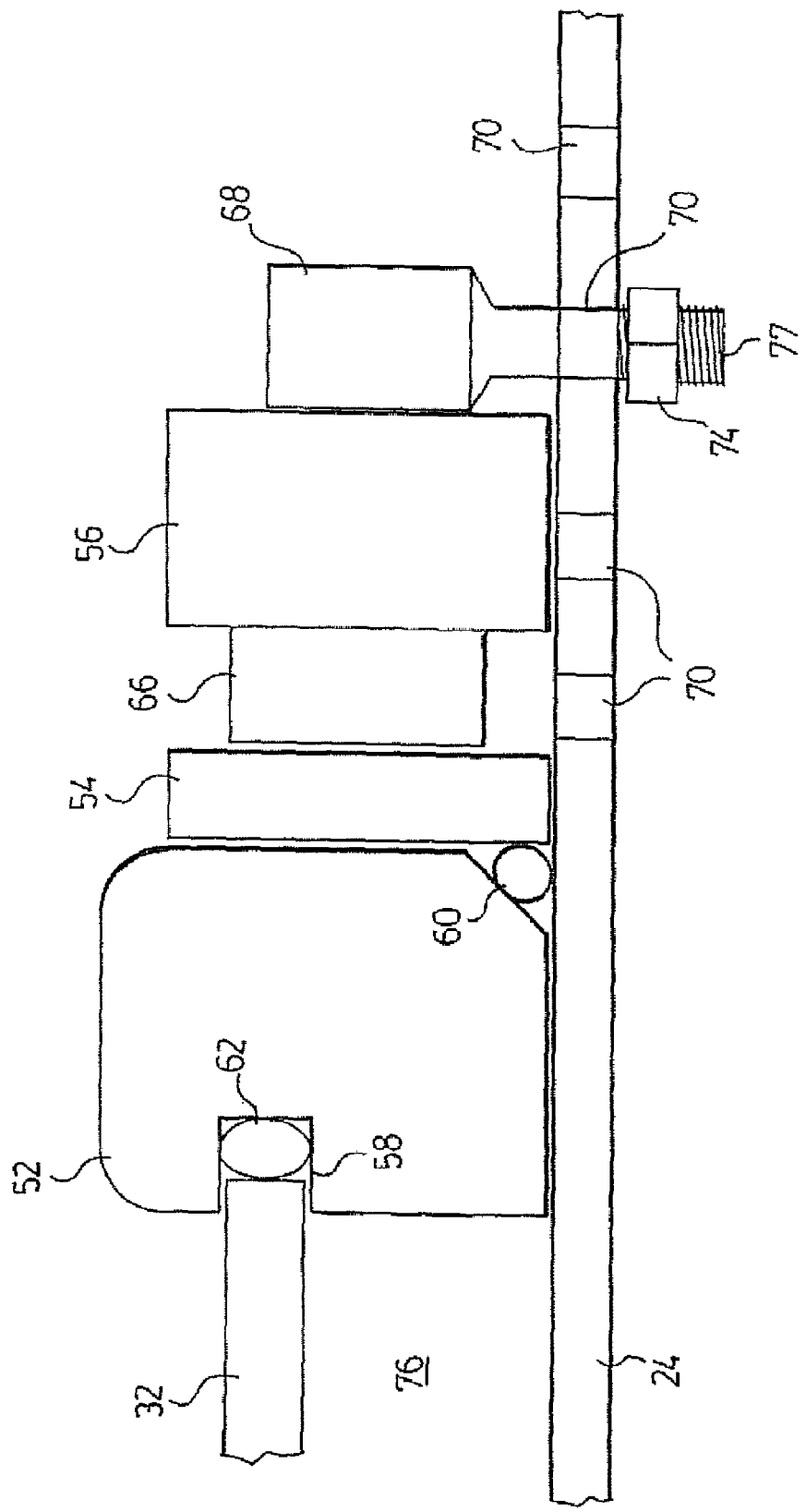
FIG. 9 is a partial side view of the second sealing device of the invention.

One or more embodiments of the invention will now be described. However, it will be understood that the following description is not intended to limit the invention to the disclosed embodiments and that various modifications will be apparent to persons skilled in the art.

With reference to FIGS. 1 to 4, the apparatus 10 of the invention includes a frame 12 having a pair of horizontal support members 14 and 16 arranged in a parallel and laterally spaced apart manner. The support members are connected by a base 18 and a support platform 20, secured, respectively, to the bottoms and tops of the horizontal support members 14 and 16. The frame 12 also includes a pair of vertical support members 21 and 22. The support members 14, 16, 20, and 22 may comprise, for example, structural "I" beams. Where necessary, the base 18 may include wheels (not shown) or other such means to facilitate movement or transportation of the apparatus.

The testing apparatus 10 includes a generally cylindrical, and preferably hollow, mandrel 24, which preferably has a length that is greater than the length of the pipe being tested. In operation, as discussed below, the mandrel is designed to be inserted into the lumen of the pipe being tested. Preferably, the mandrel has a diameter that is slightly smaller than that of the pipe being tested and is at least 18" longer than the pipe length; however, persons skilled in the art will understand that other clearances are possible after considering the following description. The mandrel 24 is provided at a first end with a first sealing device 26, which, in one embodiment, comprises a sealing plate, as described further below. In one embodiment, the first sealing device 26 is permanently secured to the mandrel 24 by, for example, welding. In another embodiment, as described further below, the sealing device 26 may be releasably attached to the mandrel. The first sealing device 26 is braced against the vertical support members 21 and 22 and may, in one embodiment, be releasably attached thereto. For example, in one embodiment, the sealing device 26 can be provided in a slot provided by support members 21 and 22 and allowed to move in a limited vertical direction with respect to the support members. As will be apparent in view of the followings description, such vertical motion serves to facilitate use of the apparatus.

The support plate 20 is provided with a plurality of support rollers 28 arranged in pairs and designed to support the mandrel 24. As noted in FIG. 4, the support rollers are designed to support the bottom of the mandrel and are angled towards each other so as to prevent the generally cylindrical mandrel from rolling off of the support rollers 28. The apparatus may also include a plurality of alignment rollers 30, also arranged in pairs, to guide and align a pipe to be tested, as will be discussed further below. Briefly, the alignment rollers are provided at the first end 14 of the mandrel to facilitate the sealing of one end of the pipe to be tested by the sealing device 26. It will be apparent that the number of alignment rollers needed will vary depending upon the specific dimensions of the apparatus and that the need number of support and alignment rollers will be apparent to persons skilled in the art. In the example shown in FIGS. 1 to 4, the apparatus includes six pairs of support rollers 28 and three pairs of alignment rollers 30. In the example illustrated in the figures, the alignment rollers are provided in two orientations where two pairs of alignment rollers are provided adjacent pairs of support rollers, to guide and support an end of the pipe being tested, while one pair of alignment rollers is provided on opposite sides of the mandrel diameter to guide or align the pipe end. Further alignment rollers can be provided as necessary.

In FIGS. 1 to 4, the pipe to be tested is indicated at 32. As shown, the pipe 32 is supported on a hoist or sling 34 or other similar mechanism. In the example shown in the figures, the sling simply comprises one or more belts 36 that are used to support the pipe, with the belts being connected to a raising and lowering mechanism, such as a crane. It will be understood that the purpose of the hoist or sling is to raise and/or support the pipe 32 and that various mechanisms can equally be used.

As shown in FIGS. 1 and 2, in use, the pipe 32 is brought into axial alignment with the mandrel 24. As indicated above, the mandrel 24 is sized so as to be able to fit within the lumen of the pipe 32. In one example, for a pipe that is fifty four inches in diameter, the mandrel is preferably fifty inches in diameter. The pipe 32 is urged over the mandrel 24 in the direction indicated by the arrow. This is further illustrated in FIGS. 5 and 6. As shown in FIG. 5, as the pipe 32 is moved towards the mandrel 24, the mandrel is slightly raised and the pipe 32 is slid between the mandrel and the support rollers 28. In one embodiment, the mandrel is provided with a plurality of skid pads 38 to facilitate the insertion of the mandrel 24 into the pipe 32. Skid pads 38 may be made of a material having a low coefficient of friction to reduce the friction between the mandrel 24 and pipe 32 during the insertion step. In one aspect, such material may comprise tetrafluroethylene, such as that marketed under the trade name Teflon®. In a preferred embodiment, and as shown in FIG. 6, the skid pads 38 may be provided with a wedge 40 to further facilitate the sliding of the pipe 32 between the mandrel 24 and the support rollers 28.

In the above discussion, reference has been made to the pipe 32 being moved over the mandrel 24. It will be understood by persons skilled in the art that the same result can be achieved by sliding the mandrel 24 into the pipe 32 while maintaining the latter in a relatively fixed position. Further, it is also possible for both the mandrel and pipe to be moved towards 13 each other.

The pipe 32 and mandrel 24 are brought together until a first end of the pipe 32 contacts the first sealing device 26. As mentioned above, the first sealing device is preferably allowed some vertical clearance with respect to support members 21 and 22 of frame 12.

FIG. 7 illustrates the mandrel 24 of the invention after insertion into a pipe 32 to be tested. Also shown is the first sealing device 26 as described previously. As mentioned above, in one embodiment, the sealing device 26 comprises a plate 42 that is of a larger diameter than the pipe 32 being tested. The plate 42 is provided with a circular groove 44 which is sized to be covered by a first end 46 of the pipe 32. A resilient seal 48, such as an "O" ring, is provided within the groove 44 so as to form a seal with the first end 46 of the pipe 32. It will be understood that the seal between the sealing plate 42 and the pipe end 46 will be formed upon forcing the plate and pipe together. This step is discussed further below. Although according to one embodiment of the invention, the first sealing device includes a solid sealing plate, it will be understood that an annular disc, which is described further in relation to FIG. 10, may also be used. Such a disc would also include the resilient seal 48 as described above.

FIG. 7 also shows the second end of the pipe 32, opposite to first end 46. As mentioned above, and as shown in FIG. 7, in one embodiment, the mandrel 24 is sized to be longer than the pipe 32 being tested. This arrangement provides sufficient mandrel surface to secure a second sealing device 50 to the mandrel 24 and, subsequently, to the pipe 32. The second sealing device 50 includes a sealing collar 52, a compression plate 54 and a force applying ring 56, each arranged in respective order from the second end of the pipe 32 extending axially away from the pipe 32. The sealing collar 52, compression plate 54 and force applying ring 56 are each generally annular bodies, each arranged in a co-axial manner over the mandrel 24.

As shown in FIG. 7 and in more detail in FIGS. 8 and 9, sealing collar 52 comprises an annular ring having a first, pipe seal groove 58 and a second mandrel seal groove 60. The pipe seal groove 58 is designed similarly to groove 44 described above, and is a generally circular groove that is sized to diameter of the second end of the pipe 32. The pipe seal groove is provided with a resilient seal 62, such as an "O" ring, and forms a seal with the second end of the pipe 32 when the two are forced together. The mandrel seal groove 60, as shown more clearly in FIG. 9, comprises a bevelled edge on the sealing collar 52. The mandrel seal groove 60 is provided on the inner diameter of the annular collar 52 and on the side opposite that adjacent the pipe 32. A resilient seal 64, such as an "O" ring or other such material, is provided in mandrel seal groove 60 and serves to provide a seal between the collar and the outer circumference of the mandrel 24. As shown in FIG. 9, such seal is created by urging the compression plate 54 is urged towards the sealing ring 52, whereby such urging causes deformation of the resilient seal 64 and tightening of the seal 64 around the circumference of the mandrel 24.

The various seals discussed above are achieved upon the urging of certain members together. As will now be described, all seals can be achieved by one urging step. Specifically, in one embodiment, and as shown in FIGS. 8 and 9, the force applying ring 56 is provided with a plurality of circumferentially spaced hydraulic rams or jacks 66, which are commonly available. The jacks 66 serve to apply pressure to the compression plate 54 as will be discussed further below. Persons skilled in the art, having referenced the present disclosure, will recognize that the hydraulic jacks 66 of the invention can be replaced with various mechanical devices that provide the required force. The jacks 66 are provided on a surface of the force applying ring 56 facing the pipe 32 to be tested. Finally, a plurality of "jack stops" 68 are provided on the outer circumference of the mandrel 24 and serve to brace the force applying ring 56. In one embodiment, the stops 68 comprise bolts that are provided through circumferentially spaced openings 70 in the mandrel. The stops 68 may include threaded portions 72 that extend through openings 70 whereby the bolts are secured to the mandrel 24 with nuts 74 that cooperate with the threaded portions of the stops 68. It will be apparent to persons skilled in the art that various alternatives to the jack stops are possible as well as various other means of securing the stops to the mandrel. For example, in another embodiment, the stops 68 may comprise anchors that are inserted into openings 70.

As shown more clearly in FIG. 9, the mandrel 24 may be provided with a number of series of openings 70, each series being located in different axial positions along the mandrel, to accommodate various lengths of pipes 32.

In use, the pipe 32 is first slid over the mandrel 24 and moved towards the first sealing device 26. The first end of the pipe, adjacent the first sealing device 26, is brought into contact with the sealing plate 42 and, more specifically, the end of the pipe 32 is aligned to overly the seal 48. Following this, the second sealing device 50 is slid over the mandrel's second end, opposite the first sealing device 26.

The second sealing device 50 is installed by first sliding the sealing ring 52, followed by the compression ring 54 and finally by the force applying ring 56. The sealing ring 52 is arranged so as to ensure that the resilient seal 62 contacts the end of the pipe 32. The second sealing device 50 is moved towards the pipe and, finally, the stops 68 are provided on the mandrel at the appropriate series of openings 70. It will be appreciated that, in one embodiment, some force may be applied to the second sealing device 50 prior to inserting the stops 68 so as to "pre-load" the apparatus. Once the stops 68 are installed and, where necessary, secured to the mandrel, the hydraulic jacks 66 are activated.

The jacks 66 serve to force the compression ring 54 and the sealing ring 52 axially towards the second end of the pipe 32. The stops 68 prevent the force applying ring 56 from moving axially away from the pipe 32. Therefore, as will be understood by persons skilled in the art, since the first end of the pipe 32 is forced towards the first sealing device 26, which is secured to the mandrel 24, the force applied by the jacks 66 results in each sealing device 26 and 50 to be forced against the respective ends of the pipe 32. Due to the presence of seals 48, 60 and 62, this, in turn, results in the formation of seals between: a) the first end of the pipe 32 and the first sealing device 26; b) the second end of the pine and the second sealing device 50; and, c) the mandrel 24 and the second sealing device 50. The result of these seals is the creation of an annular sealed space bounded by the outer surface of the mandrel 24, the inner surface of the pipe 32, and the first and second sealing device 26 and 50. This annular space is partially shown at 76 in FIG. 9

Once the sealed annular space 76 is created by attaching the two sealing devices 26 and 50, the integrity test on the pipe may be started. The test comprises filling the annular space 76 with a fluid, which is generally an incompressible fluid, and pressurizing such fluid while monitoring the pressure within the annular space 76. This method of testing will be understood by persons skilled in the art.

To fill the annular space 76, the apparatus of the invention requires a means of filling and draining or venting the annular space. FIG. 10 illustrates one embodiment of how such filling occurs, wherein like figures are indicated with the same reference numerals as above but with the letter "a" added for clarity. FIG. 10 shows another embodiment of the first sealing device at 26a. In this embodiment, the first sealing device comprises an annular disc 42a instead of the plate 42 as previously described. The disc 42a is provided with at least one opening 76 extending through the disc 42a. A port 80 extends from the opening 78 and is in fluid communication, through opening 78, into the annular space 76 that is created once the apparatus is assembled with a pipe to be tested. The port 80 is connected to a fluid filling source, not shown, using any known means, such as hoses and the like. It will be understood that any number of ports or openings can be provided on the sealing device 26a. As will be appreciated by persons skilled in the art, having at least one fill port and one vent port will facilitate the filling and voiding of the annular space 76. It will also be appreciated that it may be preferable to have one port vertically higher than the other so as to further facilitate filling and voiding of the annular space. The invention is not limited to any number or positions of the filling/venting ports. It will also be understood that although FIG. 10 depicts an embodiment wherein the first sealing device includes an annular disc, the port 80 can be provided on the plate 42 (of previous figures) as well.

FIG. 11 illustrates a further embodiment of the filling/venting system wherein a port 82 is provided on the mandrel 24. In this embodiment, the port 82 provides an opening 84 into the annular space 76 which is created between the mandrel 24 and the pipe 32 and the sealing devices (only one of which is shown for the purposes of clarity). As shown in FIG. 11, in another embodiment, both ports 80 and 82 may be provided on the same apparatus. As mentioned above, it will be understood by persons skilled in the art that it may be preferable to have one port, for example 80, to be vertically higher than the other port 82 to facilitate the fillings and venting process.

As mentioned above, a pressure gauge, not shown, is also provided on the apparatus so as to enable monitoring of the pressure within the annular space 76. In one embodiment, a further port 79 can be provided to which a pressure gauge 81 is permanently attached. In another embodiment, the source of the pressurized fluid may be provided with a pressure gauge as known in the art. Persons skilled in the art will appreciate that any means of monitoring the pressure in the annular space can be used in the invention.

It will be understood by persons skilled in the art that the apparatus of the present invention can be adapted to test pipes of any diameter or length. For example, the apparatus can be used for pipe diameters greater than three inches and for pipe lengths of one foot to one hundred feet. The upper limit of the pipe length is not necessarily limited but, as will be appreciated by persons skilled in the art, any larger length would render the apparatus of the invention very bulky and cumbersome. Furthermore, large lengths of pipe will require increased hoisting force due to the increased weight, making the testing process, although possible to conduct, difficult to manage. As described herein, one of the advantages of the present invention lies in its ability to conduct a pipe test with a minimal amount of testing fluid. Thus, to fully realize this advantage, persons skilled in the art will understand that the mandrel should be sized to be close so that its diameter is close to that of the pipe being tested. In one example, if the pipe being tested is fifty four inches in diameter, the mandrel would preferably be fifty inches in diameter. It will be understood that any dimension would still allow the apparatus of the invention to be operable.

In one embodiment, the second sealing device 50 may be removeably attached to the frame 12 of the apparatus. This aspect is illustrated in FIG. 2 wherein the second sealing device 50 is shown as optionally attached to a swing arm 51. The swing arm 51 is in turn attached to a base 53 that is rotatably attached to the frame 12. In this embodiment, when the second sealing device 50 is needed, it can simply be swung into position and attached as described above. Alternatively, the second sealing device 50 can be provided separately and still secured as described above.

In the above description, reference has been made to a first sealing sealing device, 26 or 26a, that is different in structure to the second sealing device 50. However, it will be understood that the second sealing device 50 can be used on both ends of the pipe 32 being tested.

Further, the above description has referred to the apparatus of the invention as used in a generally horizontal orientation. However, it will be understood that the apparatus can also be arranged in any orientation, for example vertical, and be equally functional. For example, referring to FIG. 1, the first sealing device 26 can form the base of the apparatus and the pipe 32 to be tested slid over the vertically extending mandrel. This type of vertical orientation may not be efficient for larger diameter pipes.

Figure 12:
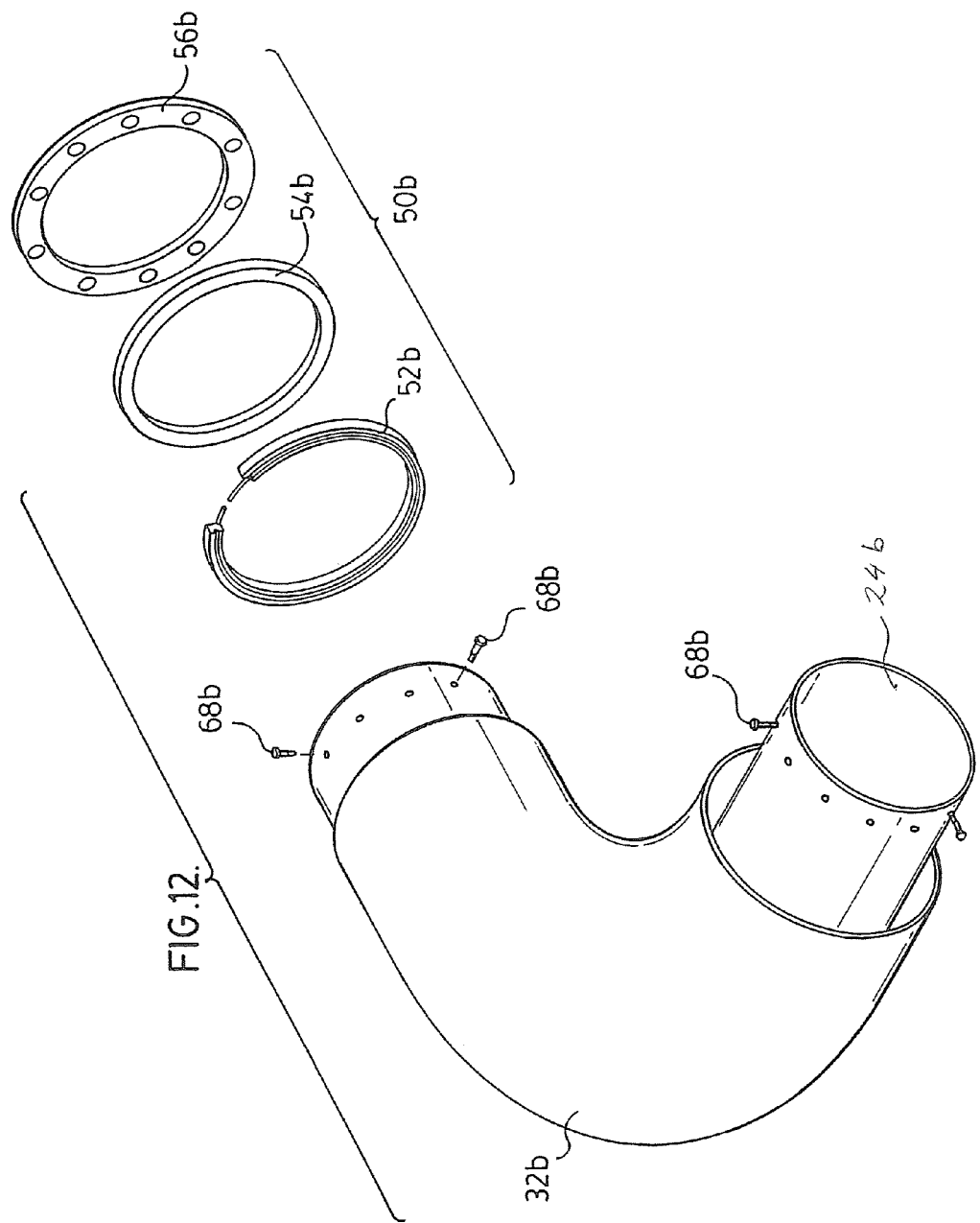
FIG. 12 is an exploded perspective view of another embodiment of the invention.

A further embodiment of the invention is illustrated in FIG. 12 wherein like elements are indicated with the suffix "b" for clarity. In FIG. 12, the pipe 32b to be tested is not linear and includes a bend. Such pipes may comprise, for example, elbows, "T" pieces, "Y" pieces etc. In such case the mandrel 24b must also include a bend. It will be appreciated that in some cases, the bend of the pipe 32b is too acute to permit a like-shaped mandrel 24b from being inserted there-through. However, where such insertion is possible, as illustrated in FIG. 12, the mandrel 24b can be provided with first and second sealing device as described above. In the embodiment of FIG. 12, it is noted that the mandrel 24b is to be provided with two alike sealing device 50b and that each is of a similar construction as the second sealing device 50 described above. It will be understood that one of the sealing devices provided on the mandrel 24b may be permanently affixed such as with first sealing device 26 and 26a discussed above.

It will be understood that the above description has focussed on a pipe 32 having a constant diameter. However, in some cases, the section of pipe to be tested may have differing internal diameters at each end. In such cases, the mandrel 24 used in the apparatus will be sized according to the minimum diameter of the pipe. The first and second sealing devices will, in turn, be sized according to the respective end of the pipe that they are to be associated with.

Another embodiment of the invention is illustrated in FIG. 13 wherein elements that are similar but not the same as those described above are identified with like reference numerals but with the letter "c" added for clarity. In this embodiment the mandrel 24 is provided with a permanently attached flange 88. As known in the art, flange 88 may comprise a generally annular disc having a generally central opening through which, one end of the mandrel 24 can be inserted. The flange 88 may be attached to the mandrel 24 by means of welds 90 or other means as known in the art. The flange 88 includes at least a pair and preferably a plurality of bolt holes through which bolts 92 are extended. The first sealing device may comprise an annular disc, or plate, 42c, which includes a complementary set of openings to accommodate the bolts 92. Nuts 94, cooperating with the bolts 92, are provided to secure and tighten the annular disc 42c to the flange 88. It will be understood that the bolts 92 may be permanently attached to either the disc 42c and/or the flange 88, thereby requiring only one end of the bolt 92 to require nuts 94. In this embodiment, the mandrel 24 of the invention can be replaced as needed without replacing the first sealing device. It will be appreciated that this functionality allows the apparatus of the invention to be quickly adapted to any diameter of pipe 32 being tested. In the embodiment of FIG. 13, the vent/fill ports 80 and 82 are shown to be similar to those of FIG. 11.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. An apparatus for testing the integrity of a pipe, said pipe having a length and first and second openings, the apparatus comprising:
    a mandrel adapted to be inserted into the pipe;
    said mandrel having first and second ends, wherein said first end is proximal to the first opening of said pipe and said second end is proximal to the second opening of said pipe;
    a first sealing device adapted to be secured to the first end of said mandrel and for sealing said first opening of the pipe;
    a second sealing device adapted to be secured to the second end of said mandrel and for sealing said second opening of the pipe;
    said second sealing device comprising: (a) an annular sealing ring, coaxially provided over said mandrel adjacent the second opening of said pipe, said sealing ring having an outer diameter greater than the diameter of the said second opening; and, (b) a means for urging the sealing ring in an axial direction against the second opening of the pipe;
    wherein said annular sealing ring includes: a first seal adapted to form a seal between said sealing ring and said second opening of the pipe; and, a second seal adapted to form a seal between said sealing ring and the outer surface of said mandrel;

wherein the means for urging the sealing ring includes two or more circumferentially spaced force applying means adapted to apply a force against said sealing ring in a direction parallel to the longitudinal axis of the pipe;

whereby, when in use, a generally annular space is created between said mandrel, said pipe, and said first and second sealing devices;

one or more ports for filling said annular space with a pressurizing fluid or for voiding said annular space of air or said fluid; and, a means for monitoring the pressure within said annular space.

2. The apparatus of claim 1 further including a compression plate located between the sealing ring and the means for urging the sealing ring, for applying evenly distributed pressure onto said sealing ring.

3. The apparatus of claim 2 wherein said force applying means comprise hydraulically operated jacks or rams.

4. The apparatus of claim 2 wherein force applying means comprise mechanically operated jacks or rams.

5. The apparatus of claim 1 wherein said mandrel is provided with stops for preventing axial movement of said means for urging in a direction away from said pipe.

6. The apparatus of claim 1 wherein said first and second seals comprise resilient sealing members.

7. The apparatus of claim 1 wherein at least one of said one or more ports are provided on at least one of said first and second sealing devices.

8. The apparatus of claim 1 wherein at least one of said one or more ports are provided on said mandrel.

9. The apparatus of claim 1 further including a frame for supporting said mandrel and said first sealing devices.

10. The apparatus of claim 9 wherein the mandrel is supported by a plurality of support rollers provided on said frame.

11. The apparatus of claim 10 wherein the mandrel is provided with a plurality of guides for guiding the pipe thereover.

12. The apparatus of claim 10 wherein the mandrel is provided with a plurality of guides for guiding the pipe thereover.

13. The apparatus of claim 9 wherein the mandrel is supported by a plurality of support rollers provided on said frame.

14. The apparatus of claim 1 wherein said first sealing device is permanently secured to said mandrel.

15. The apparatus of claim 14 wherein the first sealing device comprises a plate attached to the first end of the mandrel, said plate lying on a plane normal to the axis of the mandrel, and said plate having a surface area greater than the first opening of the pipe.

16. The apparatus of claim 1 wherein said mandrel includes a flange and wherein said first sealing device is releasably secured thereto.

17. The apparatus of claim 1 wherein said pipe includes a bend and wherein said mandrel includes a corresponding bend whereby said mandrel is insertable through said pipe.

18. The apparatus of claim 1 wherein at least one of said first and second sealing devices is permanently secured to said mandrel.

19. The apparatus of claim 1 wherein said mandrel includes a flange and wherein at least one of said first and second sealing devices is releasably secured thereto.

20. An apparatus for testing the integrity of a pipe, said pipe having a length and first and second openings, the apparatus comprising:

a mandrel adapted to be inserted into the pipe;

said mandrel having first and second ends, wherein said first end is proximal to the first opening of said pipe and said second end is proximal to the second opening of said pipe;

a first sealing device adapted to be secured to the first end of said mandrel and for sealing said first opening of the pipe;

a second sealing device adapted to be secured to the second end of said mandrel and for sealing said second opening of the pipe;

a frame for supporting the mandrel and at least one of the first and second sealing devices;

whereby, when in use, a generally annular space is created between said mandrel, said pipe, and said first and second sealing devices;

one or more ports for filling said annular space with a pressurizing fluid or for voiding said annular space of air or said fluid; and, a means for monitoring the pressure within said annular space.

21. A method for testing the integrity of a pipe, said pipe having a length and first and second openings, the method comprising:

providing a mandrel with a first end and second end and an outer diameter that is less than the inner diameter of the pipe;

the first end of the mandrel including a first sealing means;

supporting the mandrel and the first sealing means on a frame;

coaxially providing the pipe over the mandrel thereby forming an annular space between the pipe and the mandrel advancing the pipe over the mandrel until the pipe overlaps the mandrel;

providing a second sealing means adjacent the second opening of the pipe;

securing said first and second sealing means to the pipe and the mandrel to seal the annular space formed therebetween;

pressurizing the sealed annular space; and, monitoring the pressure within the sealed annular space.

22. The method of claim 21 wherein:

said first sealing means is stationary with respect to the mandrel and said second sealing means is coaxially provided over the mandrel and moveable with respect to the mandrel;

and wherein said sealed annular space is formed by urging the second sealing means against the second opening of the pipe.

* * * * *